US005976201A

United States Patent [19]

Barry et al.

[11] Patent Number: 5,976,201

[45] **Date of Patent: *Nov. 2, 1999**

[54] LOW EMISSIONS DIESEL FUEL

[75] Inventors: Edward G. Barry, Woodbury, N.J.; John N. Bennett, New Gisbourne, Australia; Dale B. Heck, West Deptford, N.J.; Peter Heinze, Wedel/Holst., Germany

[73] Assignee: Mobil Oil Corporation, Fairfax, Va.

[ * ] Notice: This patent issued on a continued prosecution application filed under 37 CFR 1.53(d), and is subject to the twenty year patent term provisions of 35 U.S.C. 154(a)(2).

[21] Appl. No.: 08/738,921

[22] Filed: Oct. 28, 1996

Related U.S. Application Data

[63] Continuation of application No. 08/444,810, May 18, 1995, abandoned, which is a continuation of application No. 08/026,793, Mar. 5, 1993, abandoned.

[51] Int. Cl.$^{6}$ .............................. C10L 1/22; C10L 1/04; C07C 7/20

[52] U.S. Cl. .............................. 44/413; 44/414; 44/418; 44/457; 585/2; 585/3; 585/4; 585/14; 208/15; 208/17

[58] Field of Search .............................. 44/413, 414, 418, 44/457; 585/2, 3, 4, 14; 208/15, 17

[56] References Cited

U.S. PATENT DOCUMENTS

| | | | |
|---|---|---|---|
| 4,482,356 | 11/1984 | Hanlon | 44/325 |
| 5,021,173 | 6/1991 | Waddoups et al. | 252/35 |
| 5,389,111 | 2/1995 | Nikanjam et al. | 44/300 |
| 5,389,112 | 2/1995 | Nikanjam et al. | 44/300 |
| 5,792,339 | 8/1998 | Russell | 208/15 |

OTHER PUBLICATIONS

J.M. Collins et al., "Better Cetane Prediction Equations Developed", Oil & Gas Journal, Jun. 7, 1982, p. 148 (PennWell).

J.M. Collins et al., "Diesel trends put new emphasis on economics and fuel quality", Oil & Gas Journal, May 31, 1982, p. 87.

Kirk–Othmer "Encyclopedia of Chemical Technology" vol. 11, pp. 682–689 (1980).

Kirk–Othmer, Encyclopedia of Chemical Technology vol. 17, p. 268 (1982).

"Development of the First CARB Certified California Alternative Diesel Fuel" by M. Nikanjam, SAE Meeting, Detroit, Mar. 1993.

State of California, Air Resources Board, Staff's proposed modifications to 13 CCR § 2256 (q), Dec. 13, 1990.

*Primary Examiner*—Mark L. Bell
*Assistant Examiner*—Patricia L. Hailey
*Attorney, Agent, or Firm*—Malcolm D. Keen

[57] ABSTRACT

A low emission diesel fuel suitable for use in underground diesel-engined mining equipment comprises a straight run distillate fuel having an end point not greater than 300° C. (about 660° F.), a cetane number in the range of 55 to 60 a specific gravity not greater than 0.83 a sulfur content not greater than 0.1 wt percent and an aromatics content of 18 to 30 wt. percent. The $T_{90}$ of the fuels is typically in the range of 255° to 270° C. (about 490° F. to 525° F.), with an initial boiling points typically in the range of 170° to 190° C. (about 340° to 374° F). Ten percent points ($T_{10}$) are typically in the range from about 200° to 220° C. (about 390° to 430° F.). The API gravity of the fuel is at least 38 and is typically in the range of 38 to 42 and the specific gravity is typically in the range of 0.82 to 0.83.

21 Claims, 2 Drawing Sheets

GC ELUTION TIME

LOW EMISSIONS DIESEL FUEL

This is a continuation of application Ser. No. 08/444,810, filed on May 18, 1995 now abandoned, which is continuation of application Ser. No. 08/026,793, filed on Mar. 5, 1993, now abandoned.

FIELD OF THE INVENTION

This invention relates to diesel fuels and more particularly to diesel fuels which produce lower levels of vehicle emissions and which are suitable for use in underground mining engines.

BACKGROUND OF THE INVENTION

A number of performance specifications have been established for diesel fuels of different grades depending upon service application. A number of different properties are set out in these specifications including, for example, flash point, cloud point, pour point, viscosity, sulfur content, distillation range, gravity and ignition quality. Of these, the ignition quality is an important parameter and is usually expressed in cetane number (CN) determined by the standard ASTM test method D613. Diesel fuels of high cetane number differ from those of lower cetane numbers by having shorter ignition lags when the fuel is injected into the cylinders of the engine. Fuels of high-cetane number also ignite at lower compressed air temperatures than the lower-cetane fuels, permitting the engine to be started at lower temperatures and to be brought to a steady running condition more quickly with less combustion knock.

Viscosity is another important characteristic of diesel fuels, affecting leakage in the fuel pump and the power required to operate the pump as well as having an influence on the size of the fuel droplets sprayed into the cylinder through the injection nozzles. Viscosity is typically expressed as kinematic viscosity, determined by ASTM test D445.

Current environmental regulations are setting stricter specifications on diesel fuels, especially in terms of sulfur content and aromatics level. Sulfur is, of course, associated with the production of acidic oxides of sulfur, a troublesome atmospheric pollutant. Aromatics are considered undesirable not only for their adverse effect on ignition quality but also because they have been implicated with the production of significant amounts of particulates in the engine exhaust.

One type of service where increasing government regulation is being proposed is in underground mines where a concern for improved air quality standards has been expressed. Although improved engine design and maintenance, increased air circulation or a reduced level of engine operations in the mines could improve air quality, each of these presents its own problems. Another solution lies in the use of fuels which result in lower levels of harmful emissions.

The present invention provides a diesel fuel which produces low levels of engine emissions and which can be readily produced in existing refineries by proper observance of product specifications coupled with suitable additive use. The present diesel fuel compositions are especially suitable for use in underground diesel-engined mining equipment and are capable of reducing all of the currently regulated emissions subject to government regulation, namely, carbon monoxide, oxides of nitrogen, unburned hydrocarbons and particulates. The properties of the present low emission fuels are low sulfur content, low final boiling range and a high but controlled emission quality.

SUMMARY OF THE INVENTION

According to the present invention diesel fuels comprise a straight run distillate fuel having an end point not greater than 300° C. (about 660° F.), a cetane number in the range of 50 to 60, e,g., in the range of 55 to 60 a specific gravity not greater than 0.83 a sulfur content not greater than 0.1 wt% and an aromatics content of 18 to 25%. These fuels are also distinguished by a number of other product characteristics which are discussed below.

DRAWINGS

In the accompanying drawings FIGS. 1 and 2 are graphs which show the results of particulate emissions testing for a low emission diesel fuel (FIG. 2) and a conventional auto-diesel fuel (FIG. 1).

DETAILED DESCRIPTION

Figure 1:
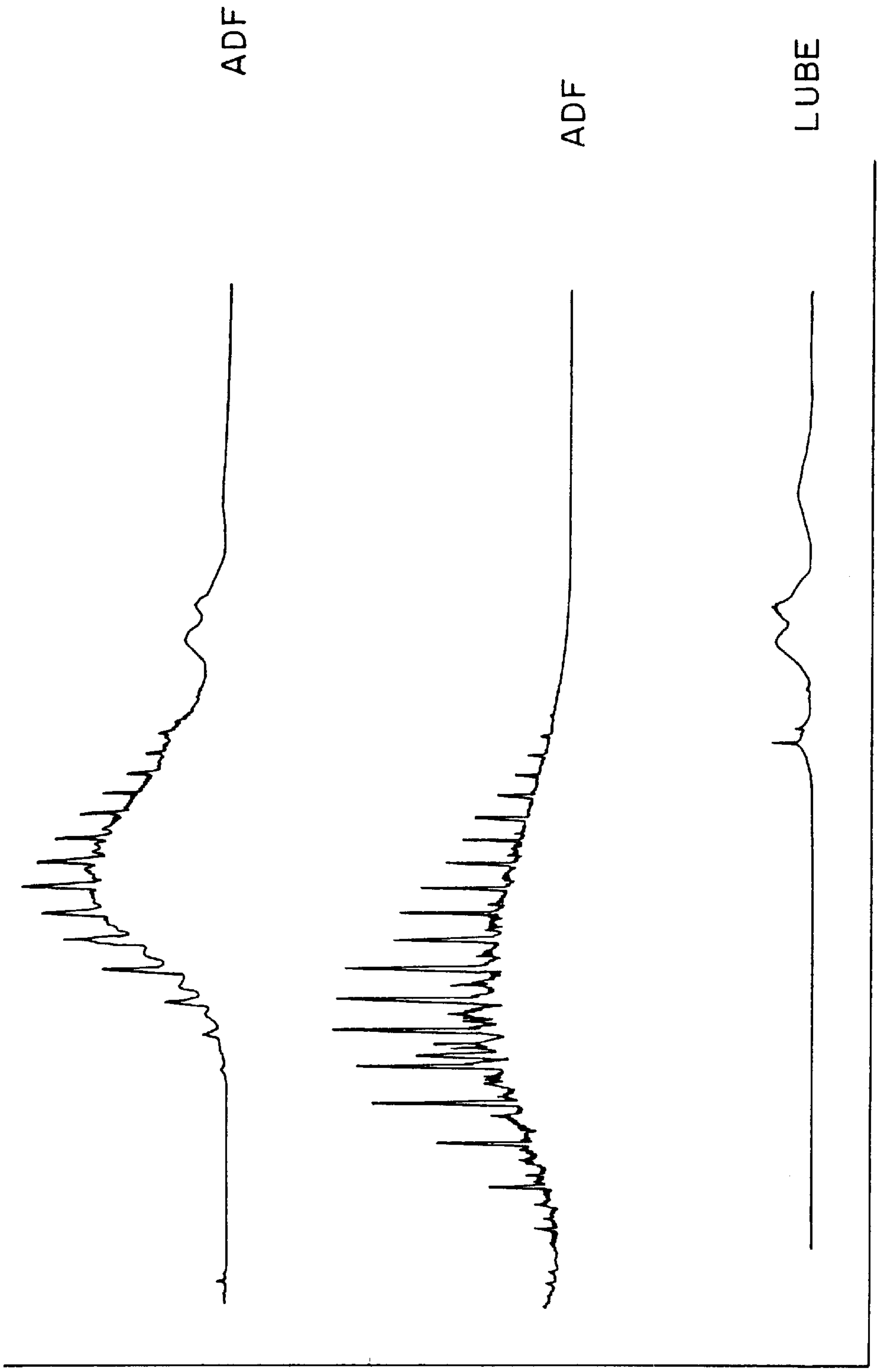

The key feature of the present diesel fuels is the high but controlled emission quality of these fuels. The cetane number is maintained in the range of 55 to 60, or of 50 to 55, preferably 55 to 58. Higher cetane numbers are considered undesirable because we have found that although gaseous emissions decrease as the cetane number increases the particulates increase. Maintaining the emission quality in the specified range therefore enables both types of emissions to be maintained at minimum values. The cetane index (ASTM D976-80) is typically in the range of 46 to 52. The cetane number of the base fuel may be improved by the use of cetane number improvers such as the alkyl nitrates e.g. octyl nitrates.

The distillation of the fuel is controlled so as to limit the density of the fuel since high densities have been found to contribute significantly to the emission of particulates. When the density is controlled in an appropriate manner, the aromatics content may extend up to about 30 weight percent or more; it has been found that the aromatics present in the controlled density, low emission fuels, mainly alkyl benzenes, naphthene benzenes and naphthalenes, are not harmful, either in terms of their effects on combustion quality or on engine emissions. The final boiling point of the fuels is therefore held below about 315° C. (600° F.) and preferably below 300° C. (572° F.). Provided that this limitation is observed, bicyclic and polycyclic aromatics will be substantially excluded. The $T_{90}$ of the fuels is typically in the range of 255° to 270° C. (about 490° F. to 525° F.).

The initial boiling points of the fuels is lower than conventional, typically in the range of 170° to 190° C. (about 340° to 374° F.). Ten percent points ($T_{10}$) are typically in the range from about 200° to 220° C. (about 390° to 430° F.). The use of the lower initial points insures that a significant amount of paraffins is present which contributes to the high cetane numbers characteristic of the present fuels. They also contribute to the characteristic high API gravity (ASTM D1298-3) of the fuels which is at least 38 and is typically in the range of 38 to 42, usually about 40. This contrasts with the lower API gravities of conventional fuels, normally in the range of 30 to 37. The specific gravity of the present fuels (ASTM D 4052-9) is, consistent with the low boiling range, lower than that of conventional fuels, typically in the range of 0.82 to 0.83, contrasting with values of about 0.84 to 0.88 for conventional fuels. Also consistent with the presence of the lower boiling materials in the fuels is a relatively low viscosity, typically from 1.7 to 1.9 cS at 40° C. (ASTM D445-3) and from about 2.4 to 2.8 at 20° C.

(ASTM D445-9). Again, this is in contrast to the higher viscosity characteristics of conventional automotive diesel fuels, which are typically about 3 to 4 cS at 40° C. It has been found, however, that the present fuels may be used in conventional injection pumps without increasing leakage or other harmful effects.

In order to reduce the level of sulfate particulates in the engine exhaust, the sulfur is held to a maximum of 0.1 wt percent and preferably below 0.05 wt percent. The use of suitable crude sources or refinery hydrotreatment, sulfur levels of 0.01 wt. percent may be attained and are desirable from the emissions standpoint. Nitrogen, by contrast, is not especially low, typically no more than 150 ppmw.

The distillate fuels are straight run i.e. not cracked, distillate stocks and this characteristic is reflected in their olefin content which is below 10 wt. percent and usually below 8 wt. percent. Saturates, by contrast, make up about 65 to 70 wt. percent of the fuel with aromatics being no more than about 35 wt. percent, usually in the range of 24 to 30 wt. percent.

Other product specifications are generally characteristic of diesel fuels for use in high speed engines, with flash point, pour point and cloud point being according to established specifications. Typically, the flash point of the present fuels is in the range of 55° to 65° C. (about 130° to 150° F.) which is in compliance with established specifications. Pour points are typically below −30° C. (below about −20° F.) and cloud points lower than −25° C. (about −15° F.).

An additive package is incorporated into the present fuels, comprising a detergent, a friction reducer and a cetane improver. Conventional materials may be used for this purpose. The detergent maintains cleanliness in the injectors and other close-tolerant components especially those close to the higher temperature areas of the engine. The friction reducer maintains long injection pump life and also assists operation of the injectors by facilitating opening of injection nozzle pintles and atomization of the fuel in the nozzle region. The cetane improver is used in its conventional role of improving combustion quality.

A number of conventional additives of these types may be used. We have found a particularly preferred combination is to use a succinimide type detergent, preferably a poly (alkenyl) succinimide. A suitable treat rate for detergents of this kind to impart the desired detergency properties is from about 60 to 80 pounds per thousand barrels (ptb), preferably about 75 ptb, although the treat rate used should be selected according to the characteristics of the detergent in actual use. A preferred detergent is a polybutenyl bis(succinimde) produced from a polybutenyl succcinic anhydride and tetraethylene pentamine (2:1 ratio, pb mol. wt. about 1200) in combination with ethylene diamine tetraacetic acid. This combination is described in U.S. U.S. Pat. No. 4,971,598.

A suitable friction reducer is typically used at a treat rate which is sufficent to confer the desired reduction in friction, typically from about 5 to 10 ptb, preferably about 7 ptb. A suitable friction reducer comprises a dimer acid having 36 carbon atoms (acid dimer of oleic acid) in combination with nonylphenol. A suitable commercial friction reducer is the one sold under the trademark Mobiladd F-800.

Conventional cetane number improvers such as the alkyl nitrates e.g. octyl nitrate, may be used in amounts appropriate to the desired ignition quality, typically from 0.1 to 5 volume percent, preferably about 1 to 2, e.g. about 1.5, volume percent.

Other additives of the kinds normally used in diesel fuels may also be present in conventional amounts to impart the desired properties to the fuel, for example, antistatic additives, antioxidants and stabilizers to improve storage stability, dyes for color etc.

The present fuels may be prepared by conventional refinery processing of suitable crudes. Being straight run products, the fuels may be produced directly by suitable fractionation after removal of contaminants in the desalter. Hydrotreating may be used if desired to reduce the sulfur level.

Product Testing

Two low emissions diesel fuels (LEDF) were prepared in two separate refineries by distillation from a paraffinic crude source (Bass Strait, Australia) and an additive package comprising a polyisobutylene succinimide detergent (treat rate 75 pounds per thousand barrels) a friction reducer (7 pounds per thousand barrels) and a cetane improver (octyl nitrate) at a rate of 1 volume percent was added. The properties of the two fuels are shown in Table 1 below.

TABLE 1

Fuel Properties

| | LEDF - 1 | LEDF - 2 |
|---|---|---|
| API Gravity | 40.6 | 40.4 |
| Density @ 15 C | 0.8226 | 0.8239 |
| Viscosity, cs. @ 20° C. | 2.5 | 2.8 |
| Viscosity, cs. @ 40° C. | 1.7 | 1.9 |
| Flash Point, ° C. (° F.) | 58 (137) | 61 (141) |
| Pour Point, ° C. (° F.) | −37 (−35) | −32 (−25) |
| Cloud Point, ° C. (° F.) | −36 (−32) | −28 (−18) |
| Nitrogen, ppm | 130 | 130 |
| Sulfur % | 0.01 | 0.06 |
| Aromatics, %, FIA-D1319-1 | 24 | 24 |
| Dilstillation Temperature, ° C. (° F.) | | |
| IBP | 177 (350) | 181 (357) |
| T10 | 205 (401) | 214 (418) |
| T50 | 232 (450) | 241 (465) |
| T90 | 259 (498) | 266 (510) |
| EP | 282 (540) | 299 (571) |
| Cetane Number | 56.4 | 59.0 |
| Cetane Index, D 976-80 | 47.8 | 50.0 |

The two fuels were tested for emissions in three different engines, a Cummins 6BT engine, a GM 6.5 liter engine with turbocharger and intercooler and a Mercedes Benz OM366LA 6 cylinder, turbocharged and intercooled engine. The Cummins and GM engines were run on the U.S. Federal Test procedure (FTP) emission cycle while the MB engine was run of the ECE R-49 test cycle used to certify heavy duty engines in Europe. The percentage improvement in emissions is shown in Table 2 below, with the improvements reported as relative to those obtained with average results from two conventional, commercial automotive diesel fuels.

TABLE 2

Improvement in Emissions

| | LEDF - 1 | | | | LDEF - 2 | | | |
|---|---|---|---|---|---|---|---|---|
| | HC | CO | NOx | Part | HC | CO | NOx | Part. |
| Cummins 6BT | | | | | | | | |
| FTP Cycle | 34 | 17 | 12 | 65 | 31 | 23 | 16 | 56 |
| Steady State | | | | | | | | |
| Idle | 15 | 14 | 12 | 19 | 26 | 25 | 11 | 28 |
| 30 mph | 8 | 4 | 1 | 54 | 14 | 11 | 5 | 54 |

TABLE 2-continued

Improvement in Emissions

| | LEDF - 1 | | | | LDEF - 2 | | | |
|---|---|---|---|---|---|---|---|---|
| | HC | CO | NOx | Part | HC | CO | NOx | Part. |
| 50 mph GM 6.5 Liter | 0 | −1 | 3 | 20 | 11 | 9 | 6 | 25 |
| FTP Cycle MB OM366LA | 31* | 16 | 7 | 28 | −8* | 36 | 7 | −2 |
| ECE R-49 | 13 | 20 | 3 | 13 | 17 | 28 | 4 | 18 |
| Average (2) | 24 | 18 | 7 | 35 | 24 | 29 | 9 | 24 |
| Ovrll Avge (2) | 24 | 24 | 8 | 29 | | | | |

(1) Improvements compared to average results from two conventional auto diesel fuels
(2) Average FTP and ECE R-49
*Not included in average As shown above, the low emission diesel fuel reduced emissions in all three test engines, using the two different test cycles. The average emissions reductions were 16 to 30% in hydrocarbons, 9 to 33% in carbon monoxide, 4 to 12% in NOx and 26 to 32% in particulates. These emissions reductions represent a significant benefit for the low emission fuels which of particular utility in underground mining environment.

Particulate Emissions

Figure 2:
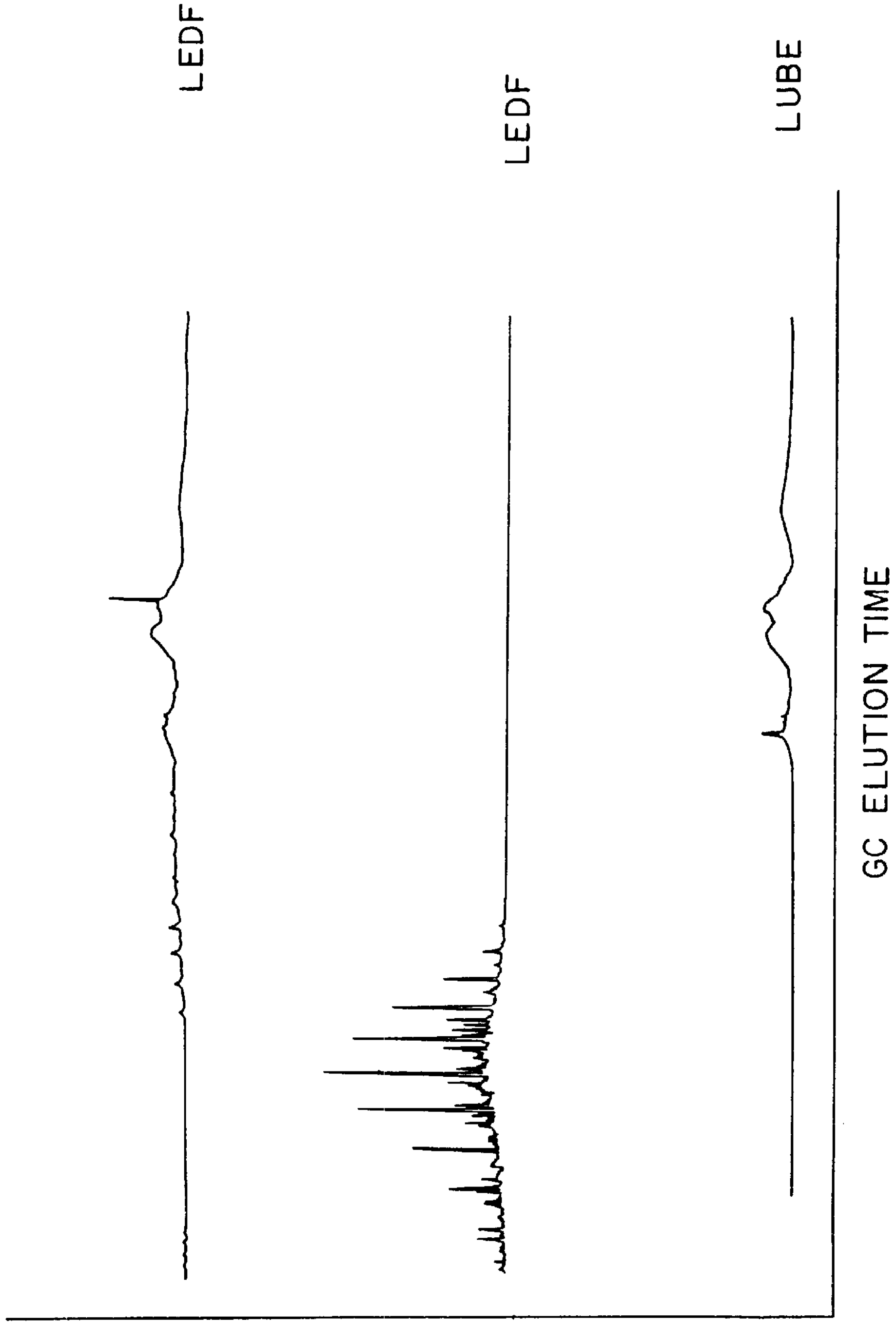

The large reduction in particulate emissions with the Cummins engine were confirmed by analysis of the particulate emissions from LEDF-1 above. The soluble organic fraction (SOF) of the particulates was extracted from the filter paper using a methylene chloride solvent. The SOF, the fuel itself and the lubricant used in the engine (Mobil 1 synthetic oil) were subjected to gas chromatography. The test methodology used for analyzing the soluble organic fraction of the particulate is described in SAE paper 870626 "Direct analysis of diesel particulate-bound hydrocarbons by gas chromatography with solid sample injection". The results are shown in FIGS. 1 and 2 of the drawings. FIG. 1 shows the curves with the low emission diesel fuel (LEDF-1) and FIG. 2 the results obtained with a conventional automotive diesel fuel. In both cases, the upper curve gives the GC analysis for the SOF, the middle curve the GC analysis for the fuel itself and the bottom curve the GC analysis for the lubricant.

The conventional automotive diesel fuel gives an SOF trace showing components from both the fuel and from the lube indicating that significant hydrocarbon emissions are caused by the use of this fuel. By contrast, the GC trace from the LEDF is almost entirely free of the fuel components, indicating a significant reduction in hydrocarbon emissions.

We claim:

1. A low emission diesel fuel having a cetane number in the range of 50 to 55, which comprises:

(i) a straight run hydrocarbon distillate having an initial boiling point in the range of 170° to 190° C., an end point not higher than 315° C., a sulfur content of less than 0.1 wt. percent and aromatics content of 18 to 30 wt. percent, a maximum specific gravity of 0.83 at 15° C., an API gravity of 38 to 43, and (ii) an additive package comprising a detergent, a friction reducing additive and a cetane number improver.

2. A diesel fuel according to claim 1 in which the initial boiling point of the distillate is in the range of 170 to 180° C.

3. A diesel fuel according to claim 1 in which the 10 percent point of the distillate is from 200° to 220° C.

4. A diesel fuel according to claim 1 in which the end point of the distillate is not greater than 300° C.

5. A fuel according to claim 1 in which the API gravity of the distillate is from 39 to 42.

6. A diesel fuel according to claim 1 in which the specific gravity of the fuel at 15° C. is from 0.82 to 0.83.

7. A diesel fuel according to claim 1 in which the maximum sulfur content is from 0.005 to 0.05 wt %.

8. A diesel fuel according to claim 6 which has a cetane number in range of 55 to 58.

9. A diesel fuel according to claim 1 in which the detergent of the additive package comprises a polyalkenyl succinimide detergent.

10. A diesel fuel according to claim 9 in which the polyalkenyl succinimide detergent comprises a polyisobutenyl succinimide.

11. A diesel fuel according to claim 1 in which the friction reducer comprises dimer acid.

12. A diesel fuel according to claim 1 in which the cetane improver comprises octyl nitrate.

13. A diesel fuel according to claim 1 in which the detergent is present in the amount of 60 to 80 pounds per 1,000 barrels of the finished fuel.

14. A diesel fuel according to claim 1 in which the friction reducer is present in the amount of 5 to 10 pounds per 1,000 barrels of the finished fuel.

15. A diesel fuel according to claim 1 having a pour point below −30° C.

16. A diesel fuel according to claim 1 having a cloud point below −25° C.

17. A diesel fuel according to claim 1 having a flash point in the range of 55 to 65° C.

18. A diesel fuel according to claim 1 in which the aromatics content is from 18 to 24 weight percent.

19. A fuel according to claim 1 in which the 90% point of the fuel is in the range of 255° to 270° C.

20. A diesel fuel according to claim 1 in which the cetane improver comprises an alkyl nitrate.

21. A diesel fuel according to claim 1 in which the aromatics content is from 24 to 30 weight percent.

* * * * *